(12) United States Patent
Drew et al.

(10) Patent No.: US 11,497,629 B2
(45) Date of Patent: Nov. 15, 2022

(54) OSSEOINTEGRATED IMPLANT ASSEMBLY HAVING TRANSVERSE THROUGH-OPENINGS, AND SYSTEMS AND METHODS OF USING SAME

(71) Applicant: University of Utah Research Foundation, Salt Lake City, UT (US)

(72) Inventors: Alex Drew, Salt Lake City, UT (US); Kent Bachus, Salt Lake City, UT (US); Erik Kubiak, Las Vegas, NV (US); Robert Tashjian, Salt Lake City, UT (US); Heath Henniger, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 23 days.

(21) Appl. No.: 16/610,938

(22) PCT Filed: May 9, 2018

(86) PCT No.: PCT/US2018/031797
§ 371 (c)(1),
(2) Date: Nov. 5, 2019

(87) PCT Pub. No.: WO2018/208913
PCT Pub. Date: Nov. 15, 2018

(65) Prior Publication Data
US 2020/0069442 A1    Mar. 5, 2020

Related U.S. Application Data

(60) Provisional application No. 62/503,542, filed on May 9, 2017.

(51) Int. Cl.
*A61F 2/78* (2006.01)
*A61B 17/72* (2006.01)
(Continued)

(52) U.S. Cl.
CPC ............ *A61F 2/78* (2013.01); *A61B 17/7241* (2013.01); *A61B 2017/564* (2013.01);
(Continued)

(58) Field of Classification Search
CPC .. A61F 2/78; A61F 2/38; A61F 2/3859; A61F 2/389; A61F 2002/7887;
(Continued)

(56) References Cited

U.S. PATENT DOCUMENTS 8,882,851 B2 * 11/2014 Smith .................... A61F 2/78
623/33
10,456,178 B2 * 10/2019 Al Muderis ....... A61B 17/7283
(Continued)

*Primary Examiner* — Yashita Sharma
(74) *Attorney, Agent, or Firm* — Ballard Spahr LLP

(57) ABSTRACT

An implant assembly for a long bone having a longitudinal axis. The implant assembly has a stem that is received in a surgically prepared medullary canal of the long bone. The stem defines at least one transverse through-opening that extends through the stem from a first portion of the outer surface of the stem to an opposed second portion of the outer surface of the stem. Each transverse through-opening has a central axis that is substantially perpendicular to the longitudinal axis of the stem. Each transverse through-opening receives a fastener and has a longitudinal dimension, measured relative to the longitudinal axis of the stem, that is sufficient to permit axial movement, relative to the longitudinal axis of the stem, of the stem relative to each fastener.

24 Claims, 12 Drawing Sheets

(51) Int. Cl.
  *A61B 17/56* (2006.01)
  *A61F 2/30* (2006.01)
  *A61F 2/60* (2006.01)
(52) U.S. Cl.
  CPC . *A61F 2002/3085* (2013.01); *A61F 2002/607* (2013.01); *A61F 2002/7887* (2013.01)
(58) Field of Classification Search
  CPC ........ A61F 2002/607; A61F 2002/2825; A61F 2002/2853; A61F 2002/2892; A61F 2002/2871; A61F 2002/2896; A61F 2002/3822; A61F 2002/3827; A61F 2002/3831; A61F 2002/3085; A61F 2002/30205; A61F 2002/30332; A61F 2002/30574; A61F 2002/30777; A61F 2002/30902; A61F 2/30; A61F 2/28; A61B 17/7241; A61B 17/72; A61B 2017/564
  See application file for complete search history.

(56) References Cited

U.S. PATENT DOCUMENTS

| | | | |
|---|---|---|---|
| 10,687,874 B2* | 6/2020 | Langdale | A61B 17/72 |
| 2007/0233104 A1* | 10/2007 | Metzinger | A61B 17/7241 606/62 |
| 2012/0330313 A1* | 12/2012 | Grady | A61B 17/7225 606/64 |
| 2014/0156022 A1* | 6/2014 | Holt | A61F 2/78 623/23.44 |
| 2015/0142125 A1* | 5/2015 | Watanabe | A61B 17/8685 623/16.11 |

* cited by examiner

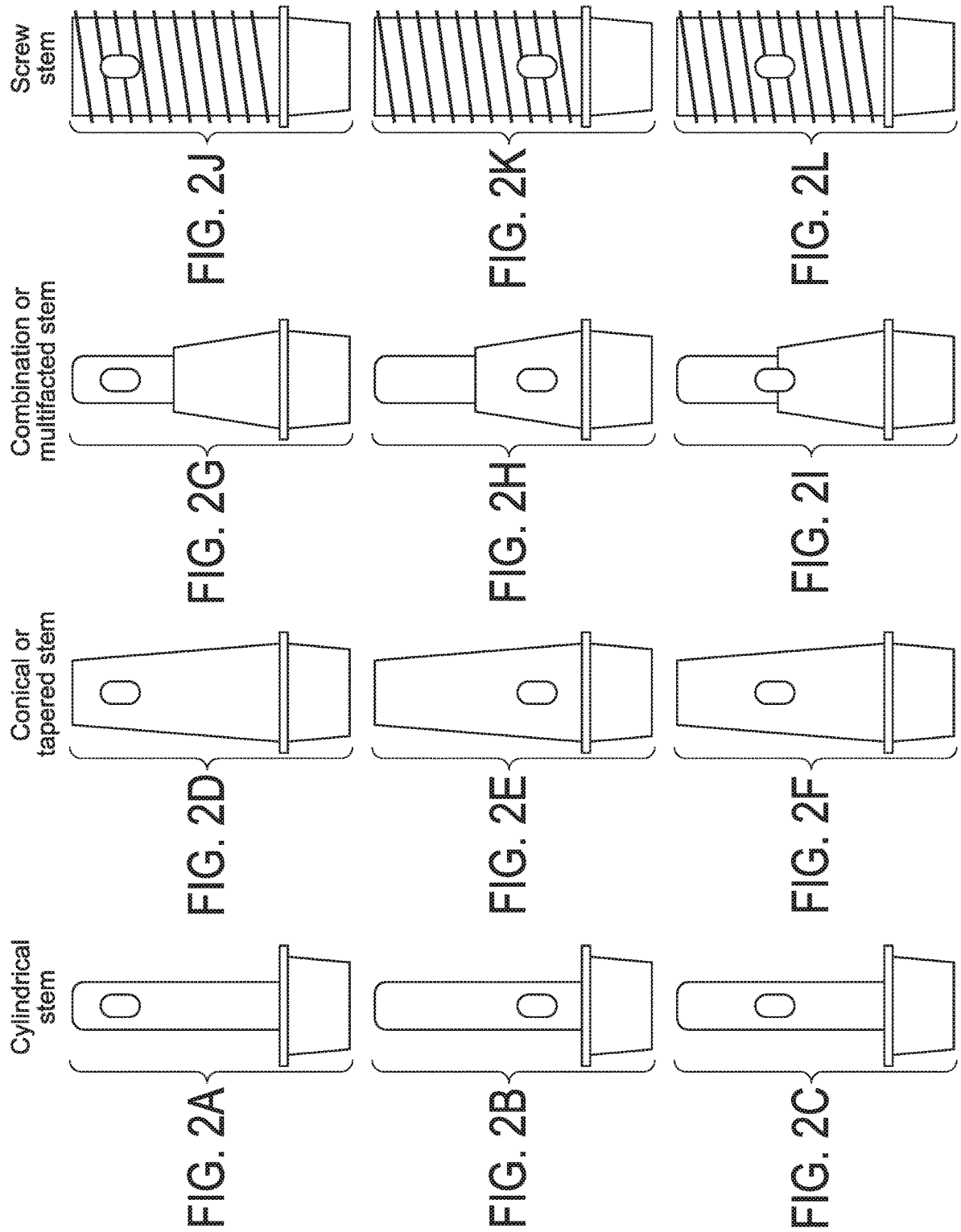

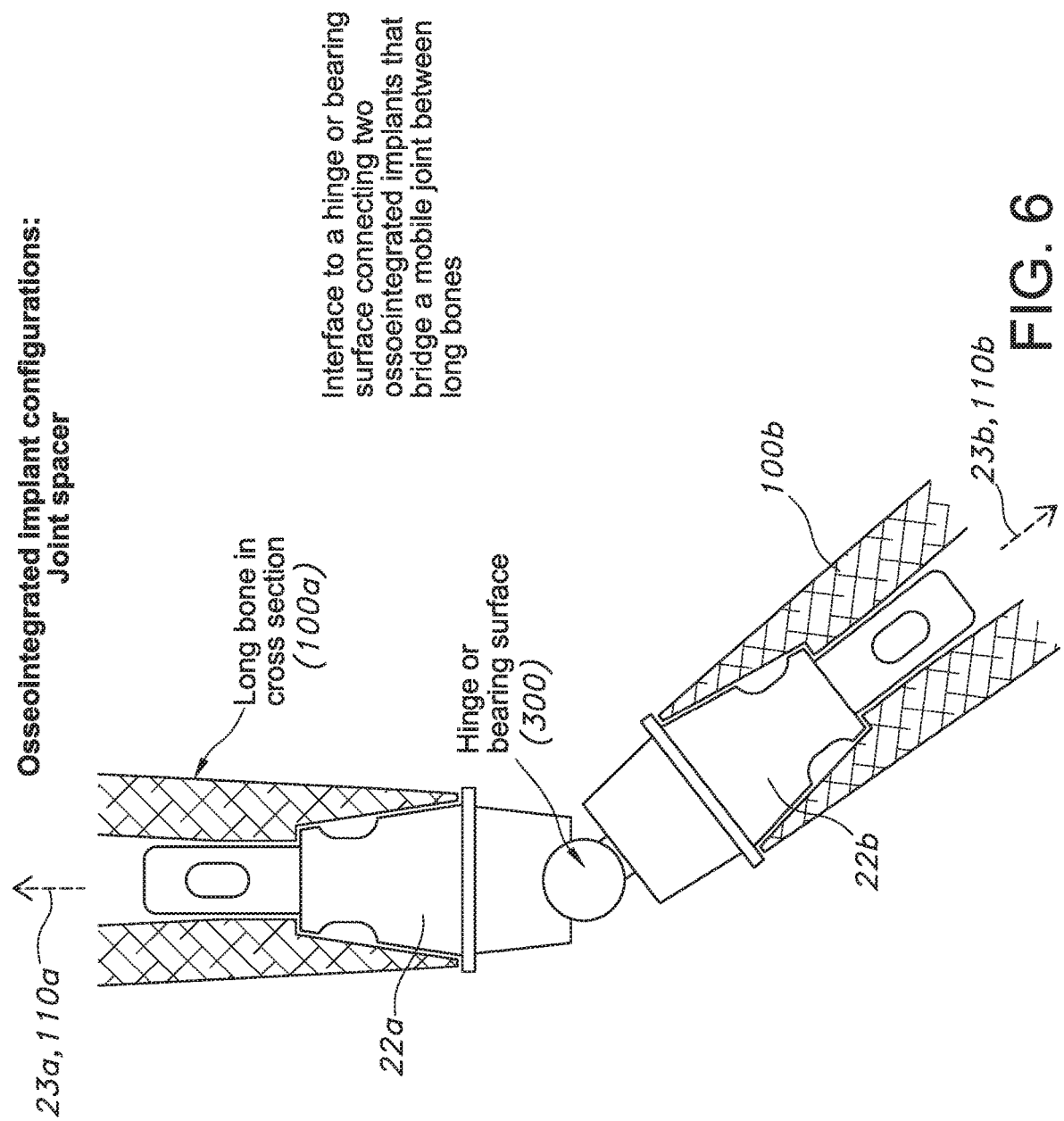

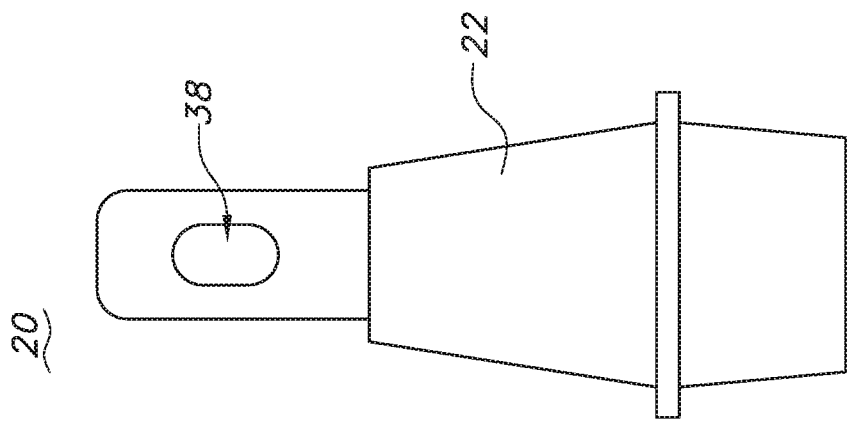
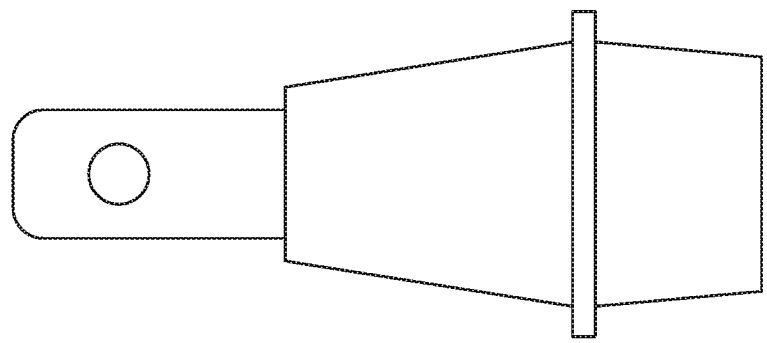
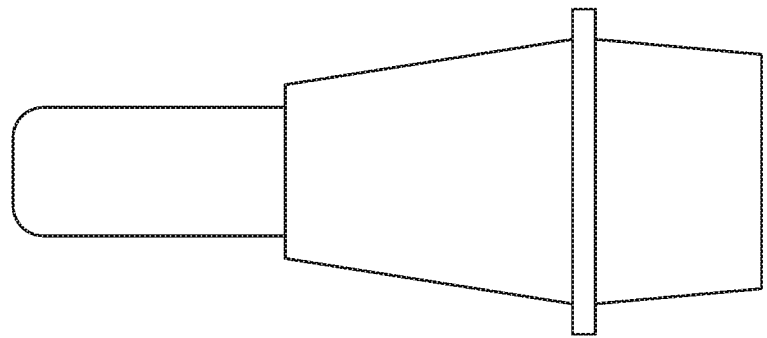
FIG. 7A

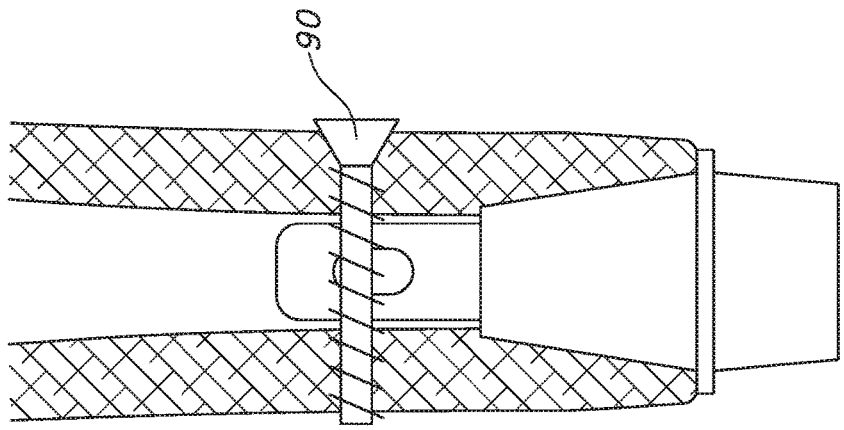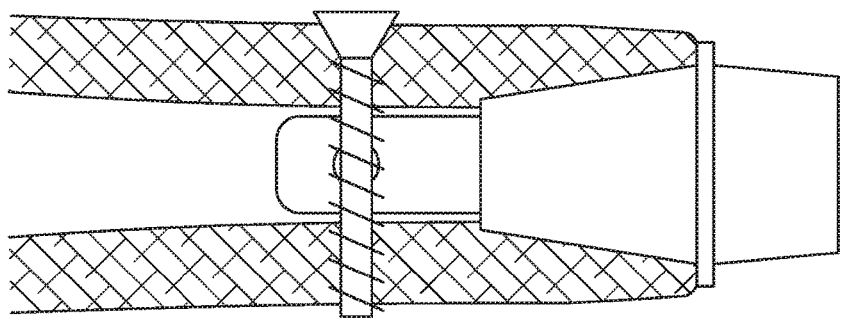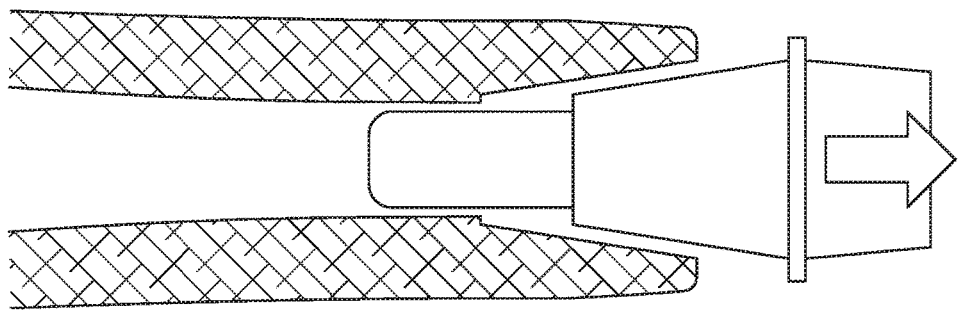
FIG. 7C

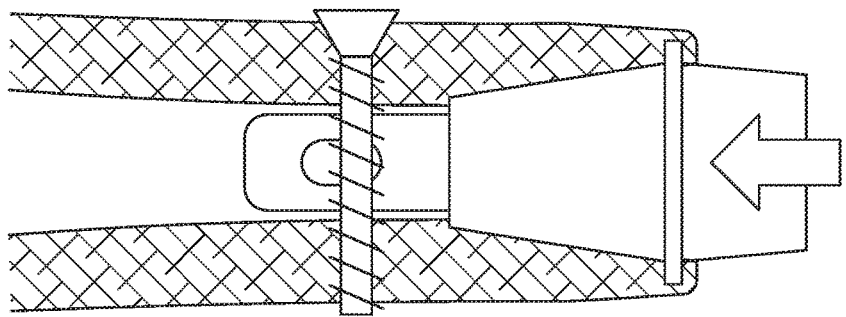
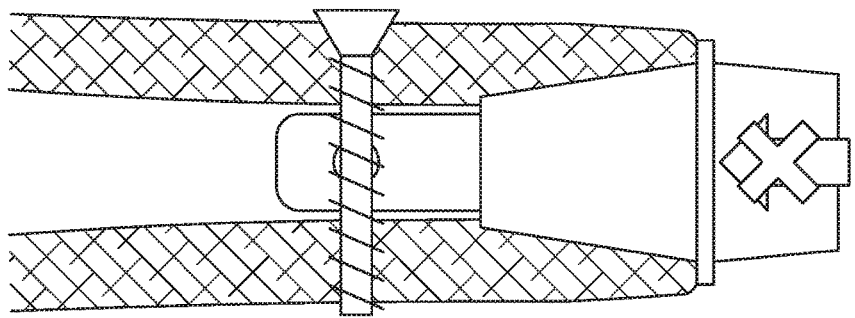
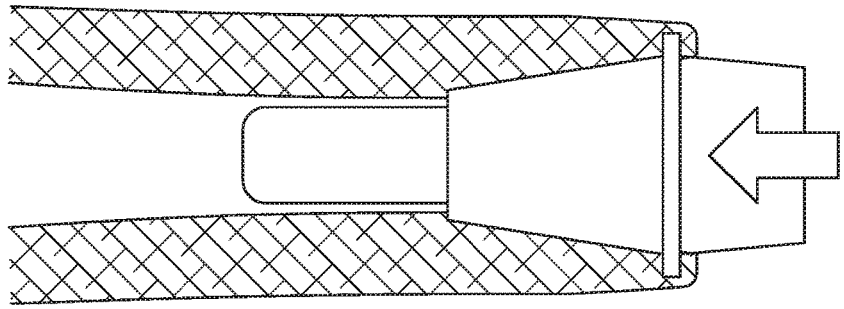
FIG. 7D

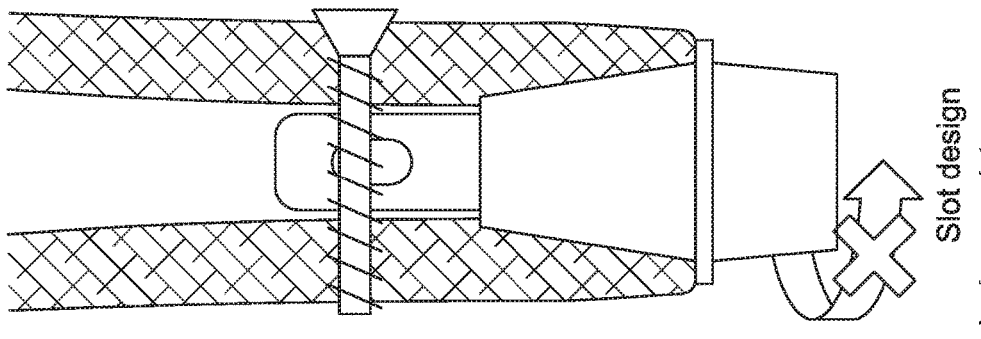
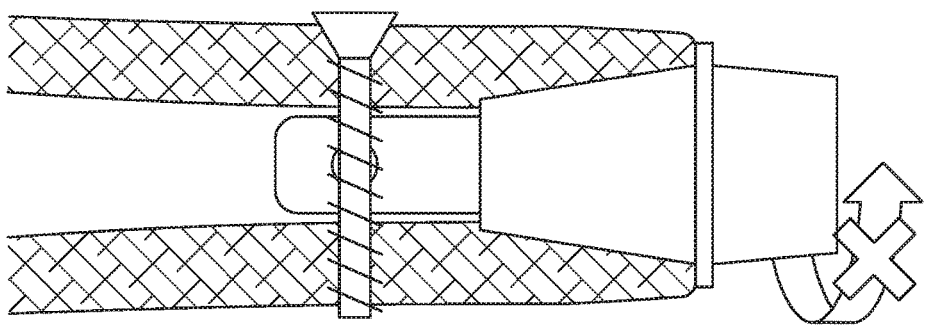
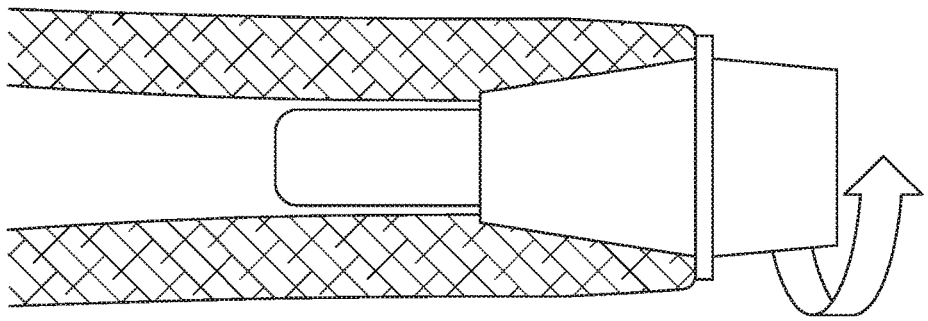
FIG. 7E

OSSEOINTEGRATED IMPLANT ASSEMBLY HAVING TRANSVERSE THROUGH-OPENINGS, AND SYSTEMS AND METHODS OF USING SAME

CROSS REFERENCE

This Application is a national stage filing under 35 U.S.C. § 371 of International Application No. PCT/US2018/031797, filed on May 9, 2018, which claims priority to and the benefit of the filing date of U.S. Provisional Patent Application No. 62/503,542, filed May 9, 2017, which are incorporated herein by reference in their entirety.

STATEMENT OF GOVERNMENT SUPPORT

This invention was made with government support under Grant W81XWH-15-C-0058 awarded by the Army/MRMC. The government has certain rights in this invention.

FIELD

This invention relates to intramedullary implant assemblies for long bones, and, more particularly, to osseointegrated implant assemblies having transverse through-openings that receive fasteners to provide intramedullary stabilization within a long bone.

BACKGROUND

Existing implant assemblies for long bones can be designed to support an implant positioned within the medullary canal of a long bone of a subject or patient. Conventionally, such implant assemblies are prone to failure under a variety of conditions, including aseptic loosening due to micromotion of the implant within the medullary canal, osteomyelitis due to poor bone ingrowth, resorption as the result of stress shielding, at the osteotomy leading to deep infection, and component failure due to mechanical fatigue.

Thus, there is a need in the pertinent art for implant assemblies that are not prone to failure under any of these conditions. In particular, as further disclosed herein, there is a need for implant assemblies that both (a) provide stabilization of the implant within the medullary canal in instances where direct implant contact or press-fit cannot be achieved; and (b) permit dynamic compressive loading at the osteotomy to stimulate bone remodeling and accommodate implant subsidence, while resisting implant motion under axial distraction, torsional, and bending loading of the implant assembly.

SUMMARY

Described herein, in various aspects, is an implant assembly for a long bone having a longitudinal axis. As further disclosed herein, the implant assembly can be configured to support an external prosthesis, to form a megaprosthesis, or to support a joint spacer. The implant assembly can comprise a stem having a longitudinal axis and an outer surface. The stem can be configured to be received in a surgically prepared medullary canal of the long bone such that the longitudinal axis of the stem is substantially aligned with the longitudinal axis of the long bone. The stem can define at least one transverse through-opening (optionally, a plurality of through-openings) that extends through the stem from a first portion of the outer surface of the stem to an opposed second portion of the outer surface of the stem. Each transverse through-opening of the at least one transverse through-opening has a central axis that is substantially perpendicular to the longitudinal axis of the stem. Each transverse through-opening of the at least one through-opening can be configured to receive a respective fastener. Each transverse through-opening of the at least one through-opening has a longitudinal dimension, measured relative to the longitudinal axis of the stem, that is sufficient to permit axial movement, relative to the longitudinal axis of the stem, of the stem relative to each fastener within the at least one transverse through-opening.

Also described herein, in other aspects, is a method comprising inserting the stem of the disclosed implant assembly within a surgically prepared medullary canal of a long bone. The method can further comprise inserting the at least one fastener through a first portion of the long bone on a first side of the surgically prepared medullary canal, through the at least one transverse through-opening of the stem, and through a second portion of the long bone on an opposed second side of the surgically prepared medullary canal. The at least one transverse through-opening of the stem of the implant assembly can be configured to permit axial movement of the implant assembly relative to the at least one fastener to accommodate subsidence of the implant assembly while resisting tensional and torsional loads.

DESCRIPTION OF THE FIGURES

FIGS. 2A-2L depict various exemplary configurations of implants having stems with a single transverse through-opening as disclosed herein.

FIGS. 2A-2C depict various configurations of implant assemblies having cylindrical stems as disclosed herein. FIG. 2A depicts a cylindrical stem having a transverse through-opening at a location proximate a first end of the stem. FIG. 2B depicts a cylindrical stem having a transverse through-opening at a location proximate a second end of the stem. FIG. 2C depicts a cylindrical stem having a transverse through-opening at an intermediate location between the first and second end portions of the stem. FIGS. 2D-2F depict various configurations of implant assemblies having conical or tapered stems as disclosed herein. FIG. 2D depicts a conical or tapered stem having a transverse through-opening at a location proximate a first end of the stem. FIG. 2E depicts a conical or tapered stem having a transverse through-opening at a location proximate a second end of the stem. FIG. 2F depicts a conical or tapered stem having a transverse through-opening at an intermediate location between the first and second end portions of the stem. FIGS. 2G-2I depict various configurations of implant assemblies having combination or multifaceted stems as disclosed herein. FIG. 2G depicts a combination/multifaceted stem having a transverse through-opening at a location proximate a first end of the stem. FIG. 2H depicts a combination/multifaceted stem having a transverse through-opening at a location proximate a second end of the stem. FIG. 2I depicts a combination/multifaceted stem having a transverse through-opening at an intermediate location between the first and second end portions of the stem. FIGS. 2J-2L depict various configurations of implant assemblies having screw stems as disclosed herein. FIG. 2J depicts a screw stem having a transverse through-opening at a location proximate a first end of the stem. FIG. 2K depicts a screw stem having a transverse through-opening at a location proximate a second end of the stem. FIG. 2L depicts a screw stem having a transverse through-opening at an intermediate location between the first and second end portions of the stem.

FIGS. 3A-3C depict various configurations of implant assemblies having cylindrical stems as disclosed herein. FIG. 3A depicts a cylindrical stem having transverse through-openings at axially spaced locations proximate a first end of the stem. FIG. 3B depicts a cylindrical stem having transverse through-openings at axially spaced locations proximate a second end of the stem. FIG. 3C depicts a cylindrical stem having transverse through-openings at two axially spaced locations positioned proximate respective opposing ends of the stem. FIGS. 3D-3F depict various configurations of implant assemblies having conical or tapered stems as disclosed herein. FIG. 3D depicts a conical or tapered stem having transverse through-openings at axially spaced locations proximate a first end of the stem. FIG. 3E depicts a conical or tapered stem having transverse through-openings at axially spaced locations proximate a second end of the stem. FIG. 3F depicts a conical or tapered stem having transverse through-openings at two axially spaced locations positioned proximate respective opposing ends of the stem. FIGS. 3G-3I depict various configurations of implant assemblies having combination or multifaceted stems as disclosed herein. FIG. 3G depicts a combination/multifaceted stem having transverse through-openings at axially spaced locations proximate a first end of the stem. FIG. 3H depicts a combination/multifaceted stem having transverse through-openings at axially spaced locations proximate a second end of the stem. FIG. 2I depicts a combination/multifaceted stem having transverse through-openings at two axially spaced locations positioned proximate respective opposing ends of the stem. FIGS. 3J-3L depict various configurations of implant assemblies having screw stems as disclosed herein. FIG. 3J depicts a screw stem having transverse through-openings at axially spaced locations proximate a first end of the stem. FIG. 3K depicts a screw stem having transverse through-openings at axially spaced locations proximate a second end of the stem. FIG. 3L depicts a screw stem having transverse through-openings at two axially spaced locations positioned proximate respective opposing ends of the stem.

FIG. 6 is a schematic diagram depicting an exemplary interface between two implant assemblies as disclosed herein to form a joint spacer that bridges a mobile joint between two long bones. As shown, the two implant assemblies can be connected at a hinge or bearing surface to permit movement at the joint.

FIG. 7A depicts a front view of three alternative configurations of an implant assembly, including a configuration without any transverse holes extending through a stem, a configuration with a single hole extending through the stem, and a configuration having a stem that defines an elongate through-opening (slot) as disclosed herein. FIG. 7C provides a schematic comparison of the performance of the no-hole stem design, the single-hole stem design, and the stem design with an elongate through-opening (slot) in response to an axial pull-out force. FIG. 7D provides a schematic comparison of the ability of the no-hole stem design, the single-hole stem design, and the stem design with an elongate through-opening (slot) to accommodate subsidence of the implant assembly relative to a long bone. FIG. 7E provides a schematic comparison of the performance of the no-hole stem design, the single-hole stem design, and the stem design with an elongate through-opening (slot) in response to a torsional force.

DETAILED DESCRIPTION

Figure 1:
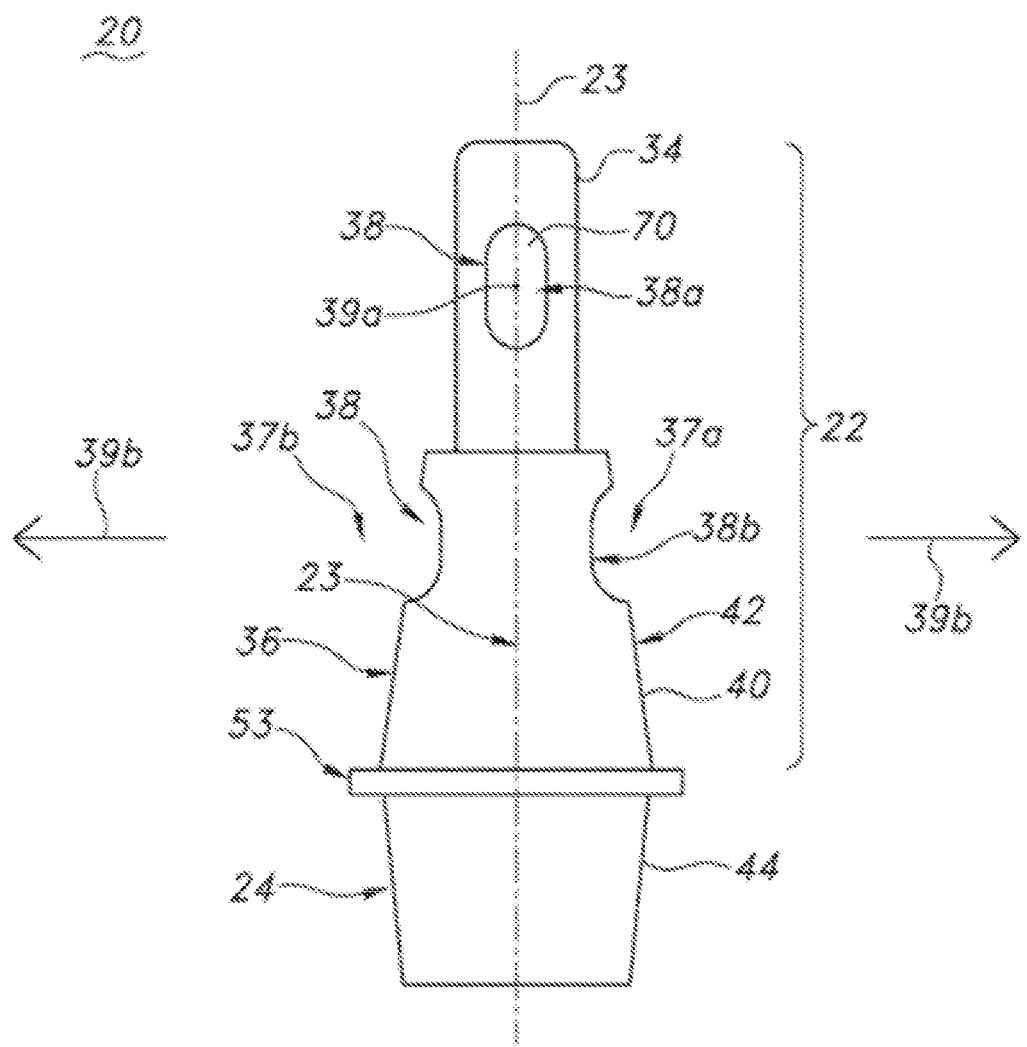
FIG. 1 is a front view of an exemplary implant having a stem with two transverse through-openings (slots) as disclosed herein.
Figure 3A:
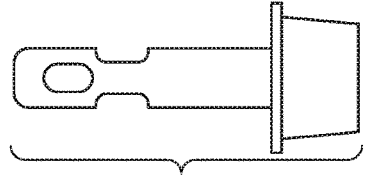
FIGS. 3A-3L depict various exemplary configurations of implant assemblies having stems with a plurality of transverse through-openings as disclosed herein.
Figure 3B:
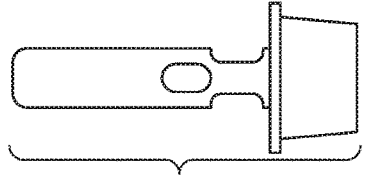
Figure 3C:
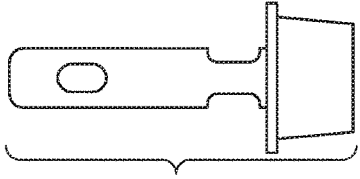
Figure 3D:
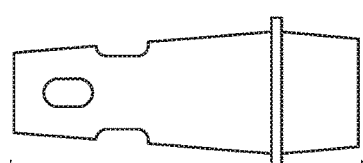
Figure 3E:
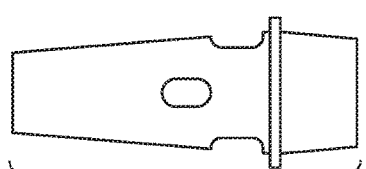
Figure 3F:
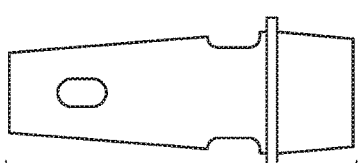
Figure 3G:
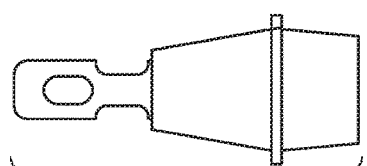
Figure 3H:
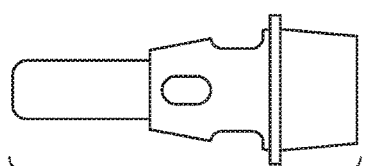
Figure 3I:
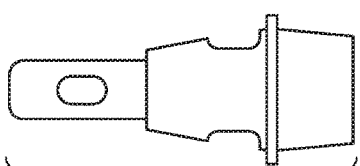
Figure 3J:
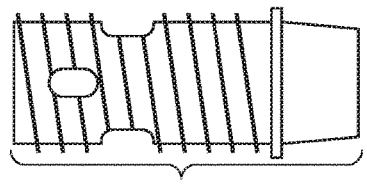
Figure 3K:
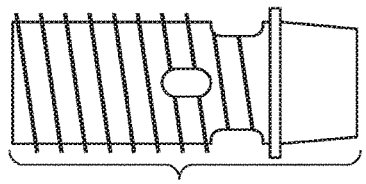
Figure 3L:
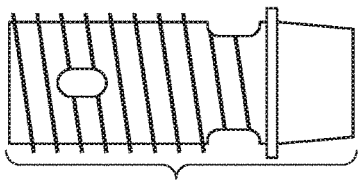

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" comprise plural referents unless the context clearly dictates otherwise. Thus, for example, reference to "a fastener" can comprise two or more such fasteners unless the context indicates otherwise.

Ranges can be expressed herein as from "about" one particular value, and/or to "about" another particular value. When such a range is expressed, another aspect comprises from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

The steps of all methods described herein can be performed in any suitable order unless otherwise specified herein or clearly indicated by context. The use of any and all examples or exemplary language (e.g., "such as") herein is intended merely to better illuminate the invention and not to place a limitation on the scope of the invention, unless otherwise indicated by the claims. Nothing in the specification should be construed as indicating any non-claimed element as essential to the practice of the invention. Ranges can be expressed herein as from "about" one particular value to "about" another particular value. Such an expression is intended to include a range from the one particular value to the other particular value, as well as ranges including variations in the particular values.

The term "subject" refers to an individual, and can include humans as well as other animals. The term "subject" does not denote a particular age or sex, and can include animals of either sex and of any age.

The term "insertional" refers to: (a) the end of a first component that is configured for insertion into a second component; (b) the direction in which a component is advanced to accomplish insertion of the component; or (c) the end of a component that is positioned closest to, or oriented in, the direction of insertion. For example, an "insertional" end of a component can be configured for insertion into a prepared site within a long bone or for insertion into an implant component. As another example, an "insertional" end of a component of an implant assembly as disclosed herein can be spaced from the opposed end of the component in the direction of insertion of the implant assembly.

The term "soft tissue" refers to tendons, ligaments, fascia, skin, fibrous tissues, fat, synovial membranes, muscles, nerves, blood vessels, and other tissues that connect, support, or surround other structures and organs of the body and that cannot be characterized as hard tissue such as bone.

As used herein, the terms "optional" or "optionally" mean that the subsequently described event or circumstance can or cannot occur, and that the description comprises instances where said event or circumstance occurs and instances where it does not.

As used herein, in some optional aspects, unless the context indicates otherwise, when values are approximated by use of the term "substantially," it is contemplated that values within up to 20%, up to 15%, up to 10%, or up to 5% (above or below) of the particular value can be included within the scope of those aspects. In further optional aspects, the included values can include the particular value modified by the term "substantially. For example, it is contemplated that the term "substantially parallel" can include aspects in which the recited elements are parallel.

The word "or" as used herein means any one member of a particular list and also comprises any combination of members of that list.

Described herein with reference to FIGS. 1-7F is an implant assembly 20 for a long bone 100 having a longitudinal axis 110. In one aspect, the implant assembly 20 can comprise a stem 22 having a longitudinal axis 23 and an outer surface 36. In exemplary aspects, the stem 22 can have a first (insertional) end portion 34 and an opposed second end portion 40. In this aspect, at least a portion of the stem 22 can be configured to be received in a surgically prepared medullary canal 112 of the long bone such that the longitudinal axis 23 of the stem 22 is substantially aligned with the longitudinal axis 110 of the long bone 100. Optionally, substantially the entire longitudinal length of the stem 22 can be received within the medullary canal 112. In other optional aspects, it is contemplated that at least a portion of the stem 22 (e.g., at least a portion of the second end portion 40 of the stem) can remain outside the long bone 100 when more proximal portions of the stem are received within the medullary canal 112.

As depicted in FIGS. 1 and 2, stem 22, including the first (insertional) end portion 34 and the second end portion 40, can be adapted to be received in a prepared hole that has been bored in the medullary cavity of a long bone, such as, for example and without limitation, a femur, a tibia, a humerus, a radius/ulna, or digit of a subject It is also contemplated that stem 22 can be securely received within the prepared hole such that the longitudinal axis 23 of the stem is substantially axially aligned with the longitudinal axis of the selected bone 110. It is contemplated that at least a portion of the outer surface 36 of the stem 22 can be treated to obtain a desired surface chemistry or roughness, thereby improving bone attachment. Optionally, the outer surface 36 of the first (insertional) portion 34 of the stem 22 can be treated to obtain the desired surface chemistry or roughness. Exemplary coatings for achieving desired surface chemistry or roughness include hydroxyapatite and/or porous coatings, such as porous titanium. Additionally, or alternatively, at least a portion of the outer surface 36 of the stem can be threaded. Optionally, stem 22 can be configured to mimic physiological properties of the anatomical bow within a native bone, thereby reducing and/or limiting torsional displacement of the stem following implantation, and improving both short-term and long-term performance of the implant assembly.

Optionally, as shown in FIGS. 2A-2C and 3A-3C, the stem 22 can have a cylindrical profile or other profile in which the outer surface 36 of the stem has a consistent outer diameter along the length of the stem. In other optional aspects, the stem 22 can have a variable outer diameter. For example, in one aspect and as shown in FIGS. 2D-2F and FIGS. 3D-3F, the stem 22 can have a conical or tapered profile, with the outer diameter of the stem decreasing moving in an insertional direction. In another exemplary aspect, and as shown in FIGS. 2G-2I and FIGS. 3G-3I, the stem 22 can have at least two distinct sections that cooperate to define a multifaceted or combination stem. For example, in this aspect, the first (insertional) end portion 34 of the stem 22 can have a first outer diameter, and the opposed second end portion 40 of the stem can have a second outer diameter that is greater than the first outer diameter. Optionally, it is contemplated that the second end portion 40 can be inwardly tapered moving in the insertional direction, while the first end portion 34 can have a consistent outer diameter. In further exemplary aspects, and as shown in FIGS. 2J-2L and FIGS. 3J-3L, the stem 22 can be threaded along at least a portion of its length (optionally, along its entire axial length).

As shown in FIGS. 1-7F, the stem 22 defines at least one transverse through-opening 38 (e.g., transverse axial slot) that extends through the stem 22 from a first portion 37*a* of the outer surface 36 of the stem 22 to an opposed second portion 37*b* of the outer surface of the stem 22. In exemplary aspects, each transverse through-opening 38 of the at least one transverse through-opening can have a central axis 39*a*, 39*b* that is substantially perpendicular to the longitudinal axis 23 of the stem 22. In these aspects, each transverse through-opening 38 of the at least one through-opening can be configured to receive a respective fastener 90. As used herein, the term "through-opening" refers to the void spaces that cooperate to define a pathway for a fastener through the entire thickness/width of a stem 22 as disclosed herein. As depicted in FIGS. 2A-3L, it is contemplated that the transverse through-openings 38 can be positioned at any desired axial location along the length of the stem 22. For example, in some configurations, at least one transverse through-opening can be positioned proximate or within the insertional end portion 34 of the stem 22. In other exemplary configurations, at least one transverse through-opening can be positioned proximate or within the second end portion 40 of the stem 22. In further exemplary configurations, at least one transverse through-opening can be positioned in an intermediate location between the first and second end portions 34, 40 of the stem 22.

In exemplary aspects, and as shown in FIGS. 7C-7F, the implant assembly can further comprise at least one fastener 90 that is configured for receipt within the at least one transverse through-opening 38 of the stem 22. Optionally, in these aspects, the at least one fastener 90 can comprise a plurality of fasteners. In some optional aspects, at least one of the fasteners can comprise a screw. In exemplary aspects, each fastener of the at least one fastener can be selected from the group consisting of a bicortical screw, a unicortical screw, a pin, or a nail.

As further disclosed herein, each transverse through-opening 38 of the at least one through-opening can have a longitudinal dimension, measured relative to the longitudinal axis 23 of the stem 22, that is sufficient to permit axial movement, relative to the longitudinal axis of the stem, of the stem relative to each fastener 90 within the at least one transverse through-opening. In operation, by permitting such axial movement of the stem relative to each fastener 90, the disclosed transverse through-openings can accommodate subsidence of the implant assembly resulting from resorption of the long bone or poor bone quality. Optionally, in contrast to an implant design in which movement of the implant assembly relative to a fastener is not permitted (see FIG. 7D, which depicts a circular opening that tightly receives a fastener), the disclosed transverse through-openings can allow the implant assembly to maintain a seal at the interface between an end of the long bone and a portion of the implant assembly positioned outside the long bone. Additionally, the transverse through-openings (e.g., slotted holes) of the implant assembly 20 disclosed herein can be configured to prevent unnecessary constraint of the implant and allow the implant to freely apply load against a transected end of the long bone under compressive forces, while still providing strength under bending, torsion, or tension loading. Although depicted as having an orientation that is generally parallel to the longitudinal axis 23 of the stem 22, it is contemplated that the transverse through-openings disclosed herein can also have any desired angular orientation relative to the longitudinal axis 23 of the stem. It is further contemplated that the through-openings disclosed herein can be positioned at any desired position relative to the circumference (outer perimeter) of the stem.

Figure 7B:
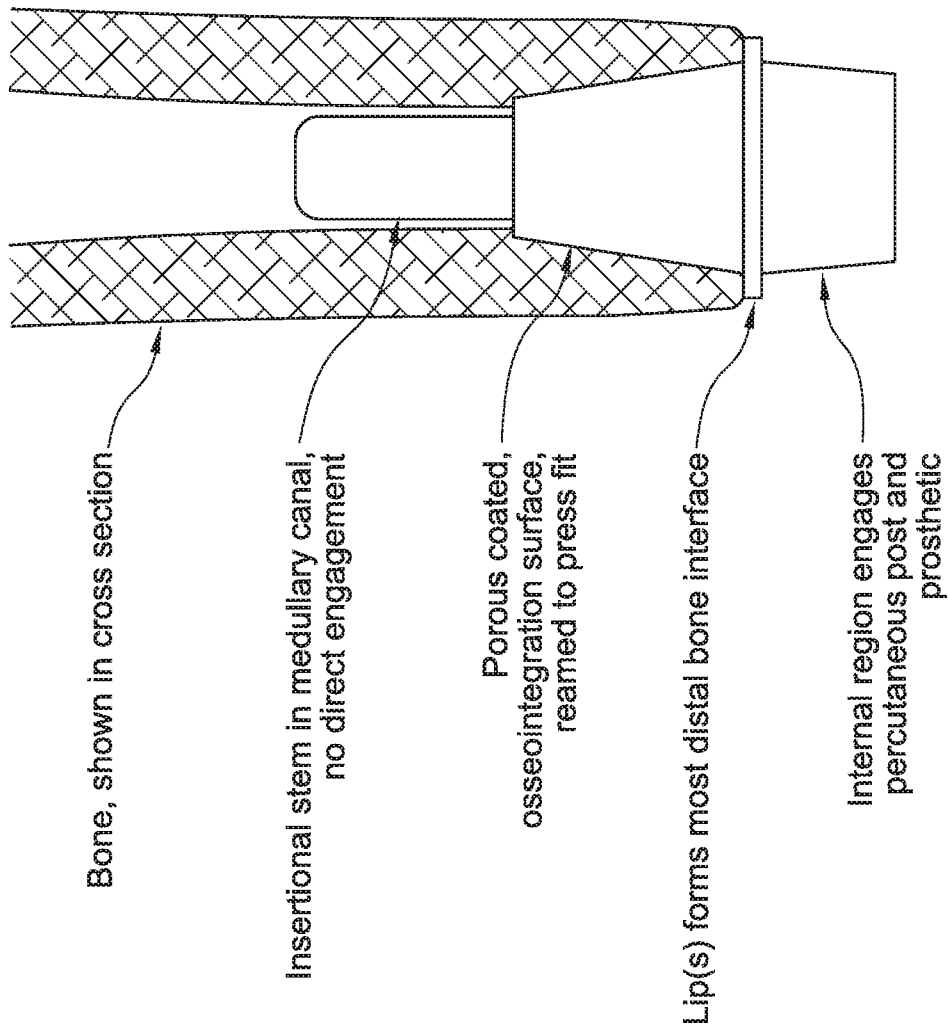
FIG. 7B is a front view of an exemplary implant assembly as disclosed herein, with the implant assembly positioned within a medullary canal of a long bone.
Figure 7F:
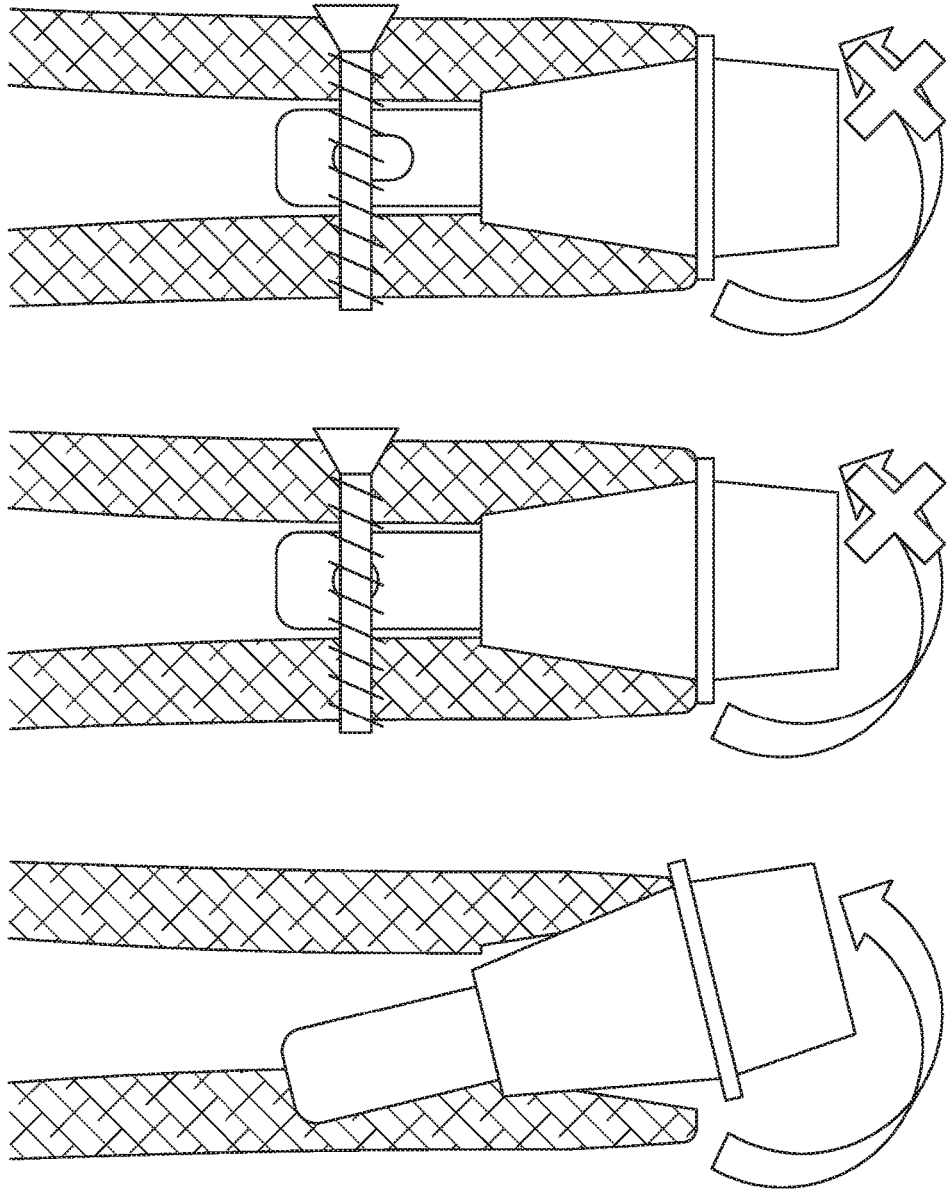
FIG. 7F provides a schematic comparison of the performance of the no-hole stem design, the single-hole stem design, and the stem design with an elongate through-opening (slot) in response to bending of the implant assembly relative to the long bone (including bone shaft fracture).

Additionally, in operation, and as shown in FIG. 7C, the at least one fastener 90 can be configured to limit distal axial movement of the implant assembly to thereby prevent removal of the implant assembly from the surgically prepared medullary canal of the long bone. In operation, and as shown in FIG. 7E, the at least one fastener 90 can limit rotation of the implant assembly relative to the longitudinal axis of the long bone, thereby increasing the mechanical connection between the implant assembly and the bone and limiting motion of the implant assembly in response to external (e.g., torsional) loading. In operation, and as shown in FIG. 7F, the at least one fastener 90 can resist bending of the implant assembly relative to the long bone. As shown in FIGS. 7C and 7E-7F, these operational characteristics cannot be achieved by existing implant designs that do not include transverse fasteners.

In additional aspects, the second end portion 40 of the stem 22 can define a surface 42 that is configured to promote bone ingrowth. It is contemplated that surface 42 can be prepared in any way (e.g., chemical treatment, surface treatment, surface contour, etc.) that is configured to promote bone ingrowth to the stem 22 and/or lip 53 as further disclosed herein. Optionally, in some aspects, the surface 42 of the second end portion 40 of the stem 22 can comprise a porous structure. This porous structure may be obtained by coating at least a portion of the second end portion 40 with a porous material using known methods for coating a substrate. Preferably, porous surface 42 comprises a continuous circumferential layer of porous material. Alternatively, porous surface 42 can comprise a plurality of porous sections that are spaced about an operative circumference of the distal end of the stem. Although not shown in the drawings, the porous surface 42 of the stem can be recessed relative to the outer surface of adjoining portions of the stem. It is contemplated that the porous surface 42 of the stem can be formed using known techniques. Optionally, porous surface 42 can comprise porous titanium, and more preferably, substantially pure porous titanium. However, it is also contemplated that other medical grade porous metals, as well as porous polymers and ceramics, can be used. Optionally, the porous surface 42 of the stem can have a thickness ranging from about 50 microns to about 2.0 mm. Optionally, the porosity of the porous surface 42 of the stem can range from about 20% to about 80% and, more preferably, from about 50% to about 70%. Optionally, the size of each pore of the porous surface 42 can range from about 25 µm to about 1,000 µm and, more preferably, from about 40 µm to about 400 µm. However, as one will appreciate, it is contemplated that the desired porosity and pore size for the porous surface 42 can be selectively varied depending upon various factors that are relevant to a particular application.

It is contemplated that, upon secure receipt of stem 22 within the surgically prepared site, the porous surface 42 of the second end portion 40 of the stem can be configured to promote integration and ingrowth of the selected bone of the subject into the stem. It is further contemplated that such osseointegration (between the selected bone and the porous surface 42 of the stem 22) can lead to improvement in the post-surgery quality of life of the subject through improved proprioception (i.e., dynamic exo-prosthesis load sensation) and efficiency (i.e., improved physiologic energy expenditure). It is also contemplated that the modular design of the implant assembly described herein can provide a platform for further optimization of the design of the stem without the need for significant surgical intervention. For example, it is contemplated that the porous region can be limited in size so as to permit removal and/or revision of the stem with minimal loss or destruction of residual bone. It is further contemplated that, in the event of a bone infection following implantation of the stem, the stem can be removed, the surgically revised site can be allowed to drain, and a therapeutic treatment regimen can be executed without significant tissue loss or harm to the subject.

In further exemplary aspects, the insertional portion 34 of the stem 22 can have a reduced outer diameter relative to the second end portion 40 of the stem, which can define a porous surface 42 as disclosed herein. In these aspects, the outer diameter of the insertional portion 34 of the stem 22 can be sufficiently small that there is no contact between the insertional portion of the stem and the inner surface of the long bone that defines the medullary canal 112. It is contemplated that such a construction can avoid impingement and undesired loading while keeping all bone growth and osseointegration at locations that are spaced away from the insertional end portion 34 (moving in opposition to the insertional direction).

Optionally, in exemplary aspects, the at least one transverse through-opening 38 can comprise a plurality of transverse through-openings. In these aspects, the plurality of transverse through-openings 38 can comprise a first transverse through-opening 38a and a second transverse through-opening 38b. Optionally, the second transverse through-opening 38b can be axially spaced from the first transverse through-opening 38a relative to the longitudinal axis 23 of the stem 22. In one optional aspect, and as shown in FIG. 1, the central axis 39a of the first transverse through-opening 38a can be substantially coplanar with the central axis 39b of the second transverse through-opening 38b (for example, with the central axes 39a, 39b extending parallel to one another and both intersecting longitudinal axis 23). Alternatively, in another optional aspect, the central axis 39a of the first transverse through-opening 38a can be angularly oriented relative to the central axis 39b of the second transverse through-opening 38b. For example, when both central axes 39a, 39b intersect longitudinal axis 23, the central axis 39b of the second transverse through-opening 38b can be angularly oriented relative to a plane containing central axis 39a and longitudinal axis 23. Optionally, in these aspects, the central axis 39a of the first transverse through-opening 38a can be substantially perpendicular to the central axis 39b of the second transverse through-opening 38b. Alternatively, the central axis 39a of the first transverse through-opening 38a can be oriented at an oblique angle (e.g., an acute or an obtuse angle) relative to the central axis 39b of the second transverse through-opening 38b.

In other exemplary aspects, the plurality of transverse through-openings can comprise first and second transverse through-openings that are positioned at the same axial location relative to the longitudinal axis 23 of the stem 22. In these aspects, it is contemplated that the central axis of the first transverse through-opening can intersect the central axis of the second transverse through-opening.

Although two transverse through-openings are depicted in the drawings, it is contemplated that any desired number of transverse through-openings can be used. It is further contemplated that the through-openings can be provided in any desired locations along the longitudinal length of the stem 22 (relative to longitudinal axis 23). For example, in some optional aspects, it is contemplated that at least one transverse through-opening (optionally, a plurality of transverse through-openings) can be defined within the insertional portion 34 of the stem 22. Optionally, in additional aspects, it is contemplated that at least one transverse through-opening (optionally, a plurality of transverse through-openings) can be defined within the second end portion 40 of the stem 22. In further optional aspects, when a porous surface 42 is provided as disclosed herein, it is contemplated that at least one transverse through-opening (optionally, a plurality of transverse through-openings) can be defined within the porous surface 42 of the stem 22. Optionally, in still further aspects, it is contemplated that the stem 22 can comprise at least one transverse through-opening (optionally, a plurality of transverse through-openings) defined in the insertional portion 34 of the stem and at least one transverse through-opening (optionally, a plurality of transverse through-openings) defined in the second end portion 40 of the stem. Optionally, the stem 22 does not comprise a through-opening extending through the porous surface 42 of the stem.

Optionally, in exemplary aspects, each transverse through-opening 38 can have an elongate shape that is configured to permit axial movement of the implant assembly relative to a fastener 90 as disclosed herein. Thus, in these aspects, it is contemplated that the length of each transverse through-opening 38 relative to longitudinal axis 23 can be greater than an outer diameter of the portion of a fastener extending through the transverse-through opening. In exemplary aspects, each transverse through-opening 38 can have an insertional end portion 70 (positioned close to the insertion direction), and each fastener 90 can be secured to the bone such that it passes through the insertional end portion 70 of a respective through-opening 38, thereby allowing the fastener 90 to apply resistance to tensile loads while allowing for dynamic compression of an osteotomy as further disclosed herein. With the fasteners 90 secured to the long bone, the fasteners can have a fixed axial position relative to the long bone as the stem of the implant assembly translates in an insertional direction or an opposed direction (opposite the insertional direction) relative to the longitudinal axis of the long bone. In exemplary aspects, a ratio between the axial length of the transverse through-opening and the outer diameter of the portion of the fastener extending through the opening can range from about 1.25:1 to about 5:1 or from about 1.5:1 to about 3:1. Actual dimensions of the transverse through-openings 38 and the fasteners 90 will depend on the particular long bone where the implant assembly is positioned. For example, femurs will be able to handle a larger diameter fastener than phalanges. Optionally, each fastener 90 can have a head portion with an outer diameter that is greater than a maximum outer diameter of the transverse through-opening that receives the fastener.

In exemplary aspects, at least one (optionally, each) transverse through-opening 38 can have an oval, substantially oval, elliptical, or substantially elliptical cross-sectional shape. In these aspects, it is contemplated that a transverse through-opening can have a major diameter extending relative to the longitudinal axis 23 of the stem (corresponding to the axial length of the opening) and a minor diameter extending perpendicular to the longitudinal axis of the stem. It is further contemplated that the major diameter can be greater than the minor diameter. Optionally, a ratio between the major diameter and the minor diameter can be at least 1.25:1. In exemplary aspects, the ratio between the major diameter and the minor diameter can range from about 1.25:1 to about 5:1 or from about 1.5:1 to about 3:1.

In further exemplary aspects, it is contemplated that the portion of the stem defining each transverse through-opening can have an outer diameter. In these aspects, it is contemplated that each through-opening can have a diameter, measured in a plane that is perpendicular to the longitudinal axis 23 of the stem 22, that is less than the outer diameter of portion of the stem defining the through-opening. For example, in some aspects, a ratio between the diameter of the through-opening and the diameter of the stem can range from about 0.3:1 to about 0.7:1.

In exemplary aspects, the implant assembly 20 can further comprise an interface component 24 having an insertional end portion 44 that is positioned adjacent to the second end portion 40 of the stem 22. In some exemplary aspects, the interface component 24 and the stem 22 can be integrally formed as a single structure or piece. Alternatively, in other exemplary aspects, the interface component 24 can be provided as a separate, discrete structure from the stem 22, and the interface component 24 can be configured for selective attachment to or detachment from the stem. In other aspects, the interface component 24 can have any structure that permits coupling to internal or external components that are needed for use of the implant assembly as disclosed herein.

Optionally, in additional aspects, the second end portion 40 of the stem 22 can have an outer diameter (outer perimeter, if not a round cross-sectional shape), and, as further described below, the insertional end portion 44 of the interface component 24 or the second end portion 40 of the stem can comprise a lip 53 that is positioned at or proximate the interface between the second end portion 40 and the interface component and that has an outer diameter that is greater than the outer diameter of the second end portion of the stem. In exemplary aspects, the lip 53 can be configured to provide a boundary between the osseointegration surface(s) of the second end portion 40 of the stem 22 and the interface component 24. Optionally, in these aspects, the lip 53 can be configured to form a seal against an end of the long bone 100.

Optionally, the interface component 24 can be hollow. Optionally, when the interface component 24 and the stem 22 are provided as separate components, a terminal portion of the second end portion 40 of stem 22 can be tapered and adapted to be received in a corresponding tapered portion of the insertional end portion 44 of the interface component. In this embodiment of the invention, it is also contemplated that the second end portion 40 of the stem can include a threaded bore (not shown) that is configured for engagement with an assembly bolt as is known in the art. In use, the lip 53, which extends radially outwardly from the second end portion 40 of the stem 22, can be adapted to engage an osteotomy created by a cut through the long bone that is generally perpendicular to the longitudinal axis of the long bone.

Optionally, the lip 53 can be configured to form a flush interface and/or seal with the selected bone. It is further contemplated that the flush interface and/or seal formed between the lip 53 and the cut bone can permit transfer of forces substantially directly to the skeletal system of the subject, thereby preventing bone atrophy. Preferably, the lip 53 can define a flat surface (on its insertional end) that extends substantially perpendicularly relative to the longitudinal axis of the stem. However, it is contemplated that the lip 53 can include a chamfered surface or have another surface shape, provided the lip permits formation of a flush interface with the cut in the bone. It is further contemplated that the lip can be shaped to substantially conform to the shape of adjacent tissues within the subject. In one embodiment, the lip can have a substantially circular cross-sectional profile about the longitudinal axis of the stem. However, it is also contemplated that the lip can have an elliptical or other cross-sectional profile that permits formation of a flush interface with the selected bone and provides desired support to the selected bone. Optionally, the outer surface of the lip 53 can be outwardly tapered, sloped, and/or curved with respect to the longitudinal axis of the stem so as to substantially conform to the shape of adjacent tissue structures within the subject. In addition, at least a portion of the surface of the lip that is adapted to abut bone can comprise an osseointegration surface (e.g., a porous material) as described herein in order to facilitate and increase bone integration, thereby ensuring contiguous load transmission between the implant assembly and the end of the bone. It is further contemplated that appropriately scaled load transmission at this interface can prevent bone resorption due to stress shielding at the bone end of the transected bone and can promote bone hypertrophy more proximally.

Although some exemplary configurations of the interface component are disclosed in detail herein, it is contemplated that the configuration of the interface component may vary. In some embodiments of the interface component, the portion below the lip is substantially cylindrical. In other embodiments, the configuration of the interface component may be tapered or concave towards its end that is oriented away from the insertional direction, or convex towards its end that is oriented away from the insertional direction. In some embodiments of the invention, the insertional end portion of the interface component includes an abutment surface that permits formation of a flush interface with the cut in the bone but does not extend radially outwardly from adjacent portions of the interface component. In other embodiments, the insertional end portion of the interface component may have a larger dimension than adjacent portions.

As further disclosed herein, implant assembly 20 can comprise a stem 22 and an interface component 24. Each of these components can be made of conventional surgical-quality metallic materials, including, for example and without limitation, titanium, cobalt chrome, and the like.

In use, the stem of the implant assembly disclosed herein can be inserted within a surgically prepared medullary canal of a long bone. The at least one fastener can be inserted through a first portion of the long bone on a first side of the surgically prepared medullary canal, the at least one transverse through-opening of the shaft of the stem, and a second portion of the long bone on an opposed second side of the surgically prepared medullary canal. As further disclosed herein, the at least one transverse through-opening of the shaft of the stem of the implant assembly can be configured to permit axial movement of the implant assembly in an insertional direction relative to the at least one fastener to accommodate subsidence of the implant assembly. As further disclosed herein, in some exemplary aspects, the second end portion of the stem can have an outer diameter, and the insertional end portion of the interface component can comprise a lip that has an outer diameter that is greater than the outer diameter of the second end portion of the stem. In these aspects, the lip can optionally form a seal against an end of the long bone.

Figure 4:
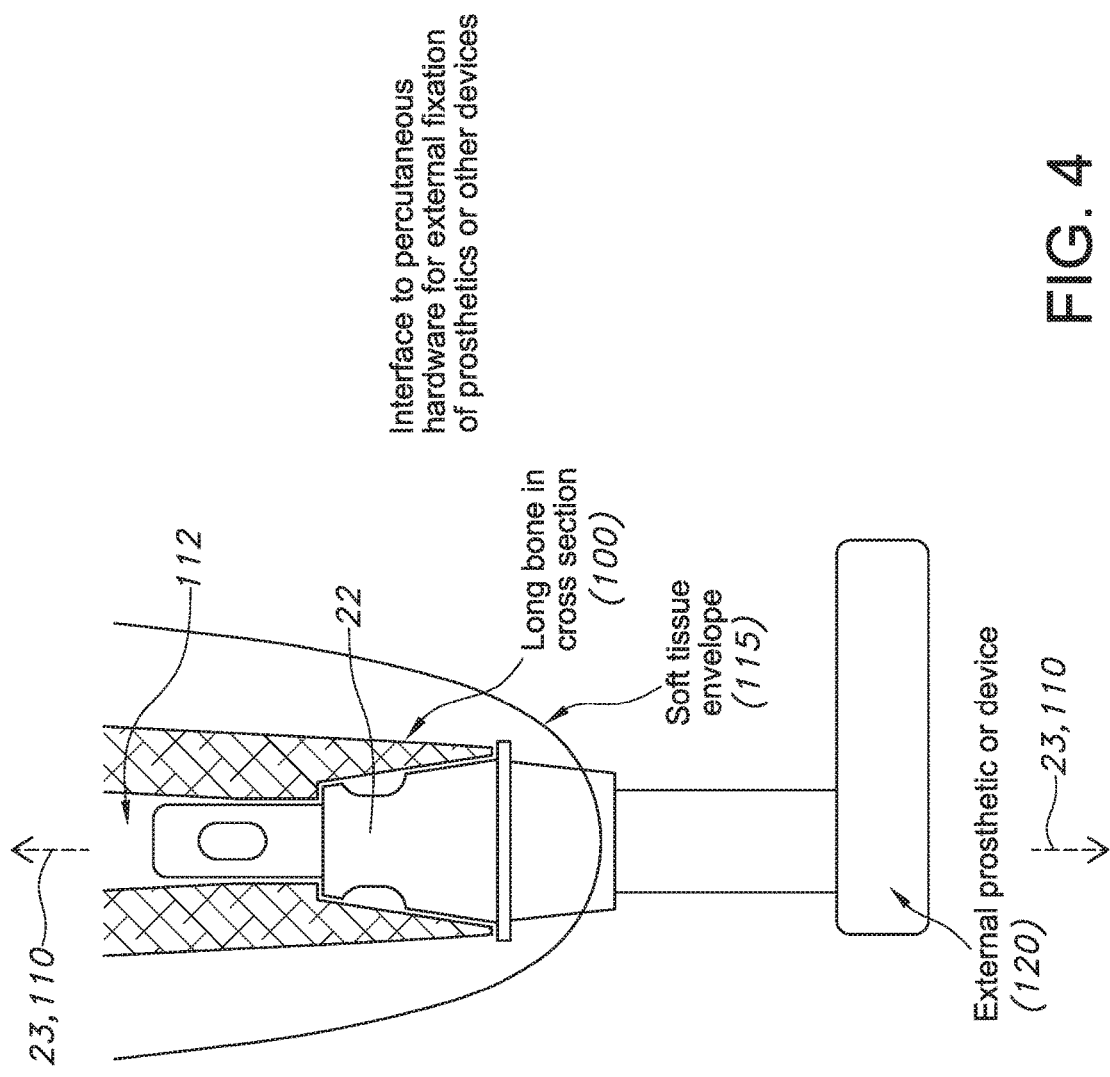
FIG. 4 is a schematic diagram depicting an exemplary interface between an implant as disclosed herein and external prosthetic (or other external device). As shown, the disclosed implant assembly can be used in a percutaneous implant/prosthetic configuration.

In exemplary non-limiting aspects, and as shown in FIG. 4, the prepared hole (medullary canal) 112 can be formed within a long bone (e.g., a femur) 100 of a subject who has had a portion of the long bone (e.g., the lower leg of the subject) amputated. In these aspects, the implant assembly described herein can be used in a method of securing an exo-prosthesis 120 to the long bone. It is contemplated that the exo-prosthesis 120 can be secured to the implant assembly using conventional techniques and components, including percutaneous posts, adapters, assembly bolts, and adapter bolts as are known in the art. As shown in FIG. 4, following positioning of the stem 22 of the implant assembly within the prepared hole 112, it is contemplated that an opposed end portion of the interface component of the implant assembly can extend beyond the soft tissue envelope 115, thereby permitting external fixation of the exo-prosthetic 120. It is contemplated that a medullary cavity of the selected bone is surgically prepared for receipt of the implant assembly. The stem and interface component can be assembled together by means of an assembly bolt or other conventional assembly mechanisms so that the stem may be positioned within the prepared site of the selected bone. Optionally, when correctly positioned within the prepared site, a lip defined by at least one of the second end portion of the stem and the insertional portion of the interface component engages an osteotomy created by a cut through the long bone that is generally perpendicular to the longitudinal axis of the long bone.

With reference to FIG. 4, upon secure receipt of the stem within the prepared site such that the longitudinal axis of the stem is substantially axially aligned with the longitudinal axis of the selected bone, the stem can be configured to promote integration of the selected bone of the subject and the interface component can be configured to promote soft tissue fixation of the subject into the assembly. More particularly, in some optional aspects, it is contemplated that the structures of these components can promote integration of bone and soft tissue of the subject into the assembly such that a seal is formed between the soft tissue of the subject and the implant assembly. It is further contemplated that the seal that is formed between the soft tissue of the subject and the implant assembly can reduce the likelihood of infection in the subject and minimize the possibility of an open path of access from the exterior to the osteotomy.

Figure 5:
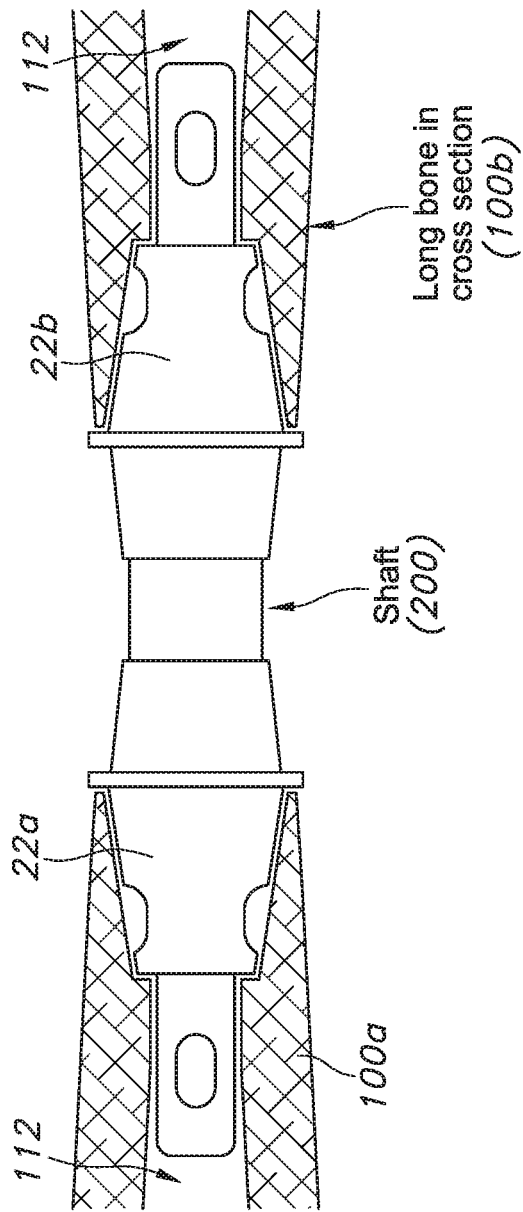
FIG. 5 is a schematic diagram depicting an exemplary interface between two implant assemblies as disclosed herein to form a megaprosthesis that bridges a gap in a long bone.

In other non-limiting aspects, and as shown in FIG. 5, first and second prepared medullary canals (holes) 112 can be formed in aligned portions 100a, 100b of a long bone that are spaced apart (or in respective long bones that are aligned with each other), and the stems 22a, 22b of first and second implant assemblies can be received within the respective first and second prepared holes. In these aspects, it is contemplated that after the stems 22a, 22b of the first and second implant assemblies are received within the respective prepared holes of the portions 100a, 100b of the long bone, the interface components 24 of the first and second implant assemblies can be joined together using a shaft 200 to form a megaprosthesis. The stems and interface components can be assembled together to the shaft by means of an assembly bolt or other conventional assembly mechanisms so that the stem may be positioned within the prepared site of the selected bone. Optionally, when correctly positioned within the prepared sites, the lips defined by at least one of the second end portions of the stems and the insertional portions of the interface components engage osteotomies created by the cuts through the long bones that are generally perpendicular to the longitudinal axes of the long bones.

In still other non-limiting aspects, and as shown in FIG. 6, first and second prepared medullary canals (holes) can be formed in first and second portions 100a, 100b of a long bone that are spaced apart (or in respective long bones that are aligned with each other), and the stems 22a, 22b of first and second implant assemblies can be received within the respective first and second prepared holes. In these aspects, it is contemplated that after the stems 22a, 22b of the first and second implant assemblies are received within the respective prepared holes of the portions 100a, 100b of the long bone, the interface components 24 of the first and second implant assemblies can be joined together using a hinge or bearing surface 300 that permits rotational and/or pivotal movement of the portions of the long bone (or respective long bones) relative to each other, thereby bridging a mobile joint to form a joint spacer. The stems and interface components can be assembled together to the hinge or bearing surface by means of an assembly bolt or other conventional assembly mechanisms so that the stem may be positioned within the prepared site of the selected bones. Optionally, when correctly positioned within the prepared sites, the lips defined by at least one of the second end portions of the stems and the insertional portions of the interface components engage osteotomies created by the cuts through the long bones that are generally perpendicular to the longitudinal axes of the long bones It is contemplated that one or more of the individual components of the implant assembly described herein can be provided in the form of a kit. It is further contemplated that the respective components of the implant assembly described herein can be labeled or color-coded to indicate the particular sizing and/or attachment features of the component that enable a surgeon or other medical practitioner to determine whether the component is appropriate use in a particular procedure and/or whether the component is complementary in size and/or function to other components of an implant assembly.

Experimental Example

An experimental comparison of the performance of the three metal implant prototypes depicted in FIG. 7A (No-Hole, Hole, and Slot) was performed. Each of the prototypes was implanted into foam blocks to simulate bone. A single screw was placed through the center of the hole in the hole design, through the upper tip of the slot in the slot design, and not used in the no-hole design. The prototypes were either pulled (tension, N=3), or twisted (rotation, N=3) out of the foam. A condition in which the implant was not fully seated at the lip 53 was simulated by leaving a gap between the prototype lip 53 and the foam, then loaded in compression (N=3). The results showed that:

In tension, the hole design and the slot design had similar performance that was significantly greater (~1.6× greater) than the no-hole design;

In rotation, the hole design and the slot design had similar performance that was significantly greater (~1.3× greater) than the no-hole design; and In compression, the no-hole design and the slot design had similar performance, but the hole design provided significantly greater resistance to movement (~1.6× greater), which prevented easy seating of the implant when the hole design was used.

Thus, unlike the other two designs, the slot design performed well in tension, rotation, and compression.

The experiment was repeating using undersized implant prototypes that had slightly smaller outer diameters that the original prototypes. The experimental results showed that:

In tension, the hole design and the slot design had similar performance that was significantly greater (~2.5× greater) than the no-hole design;

In rotation, the hole design and the slot design had similar performance that was significantly greater (~2.3× greater) than the no-hole design; and In compression, the no-hole design and the slot design had similar performance, but the hole design provided significantly greater resistance to movement (~2.5× greater), which prevented easy seating of the implant when the hole design was used.

Thus, unlike the other two designs, the undersized slot design performed well in tension, rotation, and compression.

Exemplary Aspects

In view of the described devices, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: An implant assembly for a long bone having a longitudinal axis, wherein the implant assembly is configured to support a prosthesis positioned external to the long bone, the implant assembly comprising: a stem having a longitudinal axis and an outer surface, wherein the stem is configured to be received in a surgically prepared medullary canal of the long bone such that the longitudinal axis of the stem is substantially aligned with the longitudinal axis of the long bone; and wherein the stem defines at least one transverse through-opening that extends through the stem from a first portion of the outer surface of the shaft to an opposed second portion of the outer surface of the shaft, wherein each transverse through-opening of the at least one transverse through-opening has a central axis that is substantially perpendicular to the longitudinal axis of the stem, wherein each transverse through-opening of the at least one through-opening is configured to receive a respective fastener, and wherein each transverse through-opening of the at least one through-opening has a longitudinal dimension, measured relative to the longitudinal axis of the stem, that is sufficient to permit axial movement, relative to the longitudinal axis of the stem, of the stem relative to each fastener within the at least one transverse through-opening.

Aspect 2: The implant assembly of aspect 1, wherein the at least one transverse through-opening comprises a plurality of transverse through-openings.

Aspect 3: The implant assembly of aspect 2, wherein the plurality of transverse through-openings comprise a first transverse through-opening and a second transverse through-opening that is axially spaced from the first transverse through-opening relative to the longitudinal axis of the stem.

Aspect 4: The implant assembly of aspect 3, wherein the central axis of the first transverse through-opening is substantially coplanar with the central axis of the second transverse through-opening.

Aspect 5: The implant assembly of aspect 3, wherein the central axis of the first transverse through-opening is angularly oriented relative to the central axis of the second transverse through-opening.

Aspect 6: The implant assembly of aspect 5, wherein the central axis of the first transverse through-opening is substantially perpendicular to the central axis of the second transverse through-opening.

Aspect 7: The implant assembly of any one of aspects 1-6, wherein the stem has an insertional first end portion and an opposed second end portion.

Aspect 8: The implant assembly of aspect 7, further comprising an interface component having an insertional portion that is positioned adjacent to the second end portion of the stem.

Aspect 9: The implant assembly of aspect 8, wherein the interface component and the stem are integrally formed as a single element.

Aspect 10: The implant assembly of aspect 8, wherein the interface component and the stem are separate components that are selectively attachable to and detachable from one another.

Aspect 11: The implant assembly of any one of aspects 1-10, wherein the second end portion of the stem defines a surface that is configured to promote bone ingrowth.

Aspect 12: The implant assembly of aspect 11, wherein the surface of the second end portion of the stem comprises a porous structure.

Aspect 13: The implant assembly of any one of aspects 8-12, wherein the second end portion of the stem has an outer diameter, and wherein the insertional portion of the interface component comprises a lip that has an outer diameter that is greater than the outer diameter of the second end portion of the stem.

Aspect 14: The implant assembly of aspect 13, wherein the lip is configured to form a seal against an end of the long bone.

Aspect 15: The implant assembly of any one of aspects 1-14, further comprising: at least one fastener configured for receipt within the at least one transverse through-opening of the stem.

Aspect 16: The implant assembly of aspect 15, wherein the at least one fastener comprises a plurality of fasteners.

Aspect 17: The implant assembly of aspect 15 or aspect 16, wherein each transverse through-opening of the at least one transverse through-opening has an insertional end portion, and wherein each fastener of the at least one fastener is received within the insertional end portion of a respective transverse through-opening.

Aspect 18: The implant assembly of any one of claims 15-17, wherein at least one fastener of the at least one fastener comprises a screw.

Aspect 19: The implant assembly of any one of aspects 15-18, wherein each fastener of the at least one fastener is selected from the group consisting of a bicortical screw, a unicortical screw, a pin, or a nail.

Aspect 20: A method comprising: inserting the stem of the implant assembly of any one of aspects 15-19 within a surgically prepared medullary canal of a long bone; and inserting the at least one fastener through a first portion of the long bone on a first side of the surgically prepared medullary canal, the at least one transverse through-opening of the stem, and a second portion of the long bone on an opposed second side of the surgically prepared medullary canal, wherein the at least one transverse through-opening of the shaft of the stem of the implant assembly is configured to permit axial movement of the implant assembly in an insertional direction relative to the at least one fastener to accommodate subsidence of the implant assembly.

Aspect 21: The method of aspect 20, wherein the second end portion of the stem has an outer diameter, wherein the insertional portion of the interface component comprises a lip that has an outer diameter that is greater than the outer diameter of the second end portion of the stem, and wherein the lip forms a seal against an end of the long bone.

Aspect 22: The method of aspect 20 or aspect 21, wherein each transverse through-opening of the at least one transverse through-opening has an insertional end portion, wherein each fastener of the at least one fastener is received within the insertional end portion of a respective transverse through-opening, wherein the at least one fastener is configured to limit axial movement of the implant assembly in a removal direction that is opposed to the insertional direction to thereby prevent removal of the implant assembly from the surgically prepared medullary canal of the long bone.

Aspect 23: The method of any one of aspects 20-22, wherein the at least one fastener limits rotation of the implant assembly relative to the longitudinal axis of the long bone, thereby limiting motion of the implant assembly in response to torsional loading.

Aspect 24: The method of any one of aspects 20-23, wherein the at least one fastener resists bending of the implant assembly relative to the long bone.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be comprised within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. An implant assembly for receipt into an end of a long bone having a longitudinal axis, wherein the implant assembly is configured to support a prosthesis positioned external to the long bone, the implant assembly comprising:
    a stem having a longitudinal axis and an outer surface, wherein the stem is configured to be received in a surgically prepared medullary canal of the long bone such that the longitudinal axis of the stem is substantially aligned with the longitudinal axis of the long bone, wherein the stem has an insertional end; and
    wherein the stem defines at least one transverse through-opening that extends through the stem from a first portion of the outer surface of the stem to an opposed second portion of the outer surface of the stem, wherein each transverse through-opening of the at least one transverse through-opening has a central axis that is substantially perpendicular to the longitudinal axis of the stem, wherein each transverse through-opening of the at least one through-opening is configured to receive a respective fastener, and wherein each transverse through-opening of the at least one through-opening has a longitudinal dimension, measured relative to the longitudinal axis of the stem, that is sufficient to permit axial movement, relative to the longitudinal axis of the stem, of the stem relative to each fastener within the at least one transverse through-opening, wherein each transverse through-opening of the at least one transverse through-opening is configured to permit axial movement, in an insertional direction, of the insertional end of the stem relative to the long bone along the longitudinal axis of the long bone and allow compression of the long bone from the end of the long bone to the at least one transverse opening.

2. The implant assembly of claim 1, wherein the at least one transverse through-opening comprises a plurality of transverse through-openings.

3. The implant assembly of claim 2, wherein the plurality of transverse through-openings comprise a first transverse through-opening and a second transverse through-opening that is axially spaced from the first transverse through-opening relative to the longitudinal axis of the stem.

4. The implant assembly of claim 3, wherein the central axis of the first transverse through-opening is substantially coplanar with the central axis of the second transverse through-opening.

5. The implant assembly of claim 3, wherein the central axis of the first transverse through-opening is angularly oriented relative to the central axis of the second transverse through-opening.

6. The implant assembly of claim 5, wherein the central axis of the first transverse through-opening is substantially perpendicular to the central axis of the second transverse through-opening.

7. The implant assembly of claim 1, wherein the stem has a first end portion and an opposed second end portion, and wherein the implant assembly further comprises an interface component having an insertional portion that is positioned adjacent to the second end portion of the stem.

8. The implant assembly of claim 7, wherein the interface component and the stem are integrally formed as a single element.

9. The implant assembly of claim 7, wherein the interface component and the stem are separate components that are selectively attachable to and detachable from one another.

10. The implant assembly of claim 1, wherein the second end portion of the stem defines a surface that is configured to promote bone ingrowth.

11. The implant assembly of claim 10, wherein the surface of the second end portion of the stem comprises a porous structure.

12. The implant assembly of claim 7, wherein the second end portion of the stem has an outer diameter, and wherein the insertional portion of the interface component comprises a lip that has an outer diameter that is greater than the outer diameter of the second end portion of the stem.

13. The implant assembly of claim 12, wherein the lip is configured to form a seal against the end of the long bone.

14. The implant assembly of claim 1, further comprising:
    at least one fastener configured for receipt within the at least one transverse through-opening of the stem.

15. The implant assembly of claim 14, wherein the at least one fastener comprises a plurality of fasteners.

16. The implant assembly of claim 14, wherein each transverse through-opening of the at least one transverse through-opening has an insertional end portion, and wherein each fastener of the at least one fastener is received within the insertional end portion of a respective transverse through-opening.

17. The implant assembly of claim 14, wherein at least one fastener of the at least one fastener comprises a screw.

18. The implant assembly of claim 14, wherein each fastener of the at least one fastener is selected from the group consisting of a bicortical screw, a unicortical screw, a pin, or a nail.

19. A method comprising:
    inserting the stem of the implant assembly of claim 14 within a surgically prepared medullary canal of a long bone; and
    inserting the at least one fastener of the implant assembly through a first portion of the long bone on a first side of the surgically prepared medullary canal, the at least one transverse through-opening of the stem, and a second portion of the long bone on an opposed second side of the surgically prepared medullary canal,
    wherein the at least one transverse through-opening of the shaft of the stem of the implant assembly is configured to permit axial movement of the implant assembly in the insertional direction relative to the at least one fastener to accommodate subsidence of the implant assembly.

20. The method of claim 19, wherein the stem has a first end portion and an opposed second end portion, wherein the implant assembly comprises an interface component having an insertional portion that is positioned adjacent to the second end portion of the stem, wherein the second end portion of the stem has an outer diameter, wherein the insertional portion of the interface component comprises a lip that has an outer diameter that is greater than the outer diameter of the second end portion of the stem, and wherein the lip forms a seal against the end of the long bone.

21. The method of claim 19, wherein each transverse through-opening of the at least one transverse through-opening has an insertional end portion, wherein each fastener of the at least one fastener is received within the insertional end portion of a respective transverse through-opening, and wherein the at least one fastener is configured to limit axial movement of the implant assembly in a removal direction that is opposed to the insertional direction to thereby prevent removal of the implant assembly from the surgically prepared medullary canal of the long bone.

22. The method of claim 19, wherein the at least one fastener limits rotation of the implant assembly relative to the longitudinal axis of the long bone, thereby limiting motion of the implant assembly in response to torsional loading.

23. The method of claim 19, wherein the at least one fastener resists bending of the implant assembly relative to the long bone.

24. The implant assembly of claim 1, wherein at least a portion of the outer surface of the stem is threaded.

\* \* \* \* \*